United States Patent
Klimoski

Patent Number: 5,865,783
Date of Patent: Feb. 2, 1999

[54] PHYSIOLOGY BASED WRIST SUPPORT

[76] Inventor: David B. Klimoski, P.O. Box 21641, Concord, Calif. 94521

[21] Appl. No.: 814,788

[22] Filed: Mar. 10, 1997

Related U.S. Application Data

[60] Provisional application No. 60/016,854 May 3, 1996.
[51] Int. Cl.⁶ .............................. A61F 5/00; A61F 13/00; A61F 5/37
[52] U.S. Cl. ................. 602/64; 602/21; 602/22; 128/879
[58] Field of Search ............. 602/60–64, 20–22, 602/5; 128/878–880; 2/16, 18–20, 161.1, 161.2, 162

[56] References Cited

U.S. PATENT DOCUMENTS

| | | | |
|---|---|---|---|
| D. 259,955 | 7/1981 | Helferich | 602/21 X |
| 1,227,700 | 5/1917 | Tucker | 602/21 |
| 1,554,807 | 9/1925 | Gately et al. | 2/18 |
| 2,284,300 | 5/1942 | Portal | 2/18 |
| 3,703,171 | 11/1972 | Schiavitto | 602/63 X |
| 3,774,242 | 11/1973 | Owen | 602/21 X |
| 4,290,147 | 9/1981 | Brückner et al. | 2/18 |
| 4,531,241 | 7/1985 | Berger | 2/161 R |
| 4,829,604 | 5/1989 | Allen et al. | 2/170 |
| 4,850,341 | 7/1989 | Fabray | 128/44 |
| 4,883,073 | 11/1989 | Aziz | 128/878 |
| 4,899,763 | 2/1990 | Sebastian et al. | 128/878 |
| 4,941,460 | 7/1990 | Working | 128/77 |
| 4,961,418 | 10/1990 | McLaurin-Smith | 602/61 X |
| 4,977,890 | 12/1990 | Mann | 602/21 |
| 5,003,967 | 4/1991 | McConnel | 128/77 |
| 5,014,689 | 5/1991 | Meunchen et al. | 128/77 |
| 5,058,573 | 10/1991 | Hess et al. | 128/77 |
| 5,152,740 | 10/1992 | Harkensee et al. | 602/13 |
| 5,160,314 | 11/1992 | Peters | 602/21 |
| 5,203,766 | 4/1993 | Carter et al. | 602/21 |
| 5,205,812 | 4/1993 | Wasserman | 602/5 |
| 5,217,029 | 6/1993 | Shields | 602/62 X |
| 5,254,078 | 10/1993 | Carter et al. | 602/21 |
| 5,256,136 | 10/1993 | Sucher | 602/21 |
| 5,353,440 | 10/1994 | Meldeau | 2/161.1 |
| 5,358,471 | 10/1994 | Klotz | 602/21 |
| 5,370,606 | 12/1994 | Martel et al. | 602/64 |
| 5,376,066 | 12/1994 | Phillips et al. | 602/21 |
| 5,385,537 | 1/1995 | Davini | 602/21 |
| 5,397,296 | 3/1995 | Sydor et al. | 602/21 |
| 5,409,451 | 4/1995 | Daneman | 602/21 |
| 5,413,553 | 5/1995 | Downes | 602/21 |
| 5,417,645 | 5/1995 | Lemmen | 602/21 |
| 5,421,811 | 6/1995 | More et al. | 602/21 |
| 5,437,620 | 8/1995 | Shelly | 602/21 |
| 5,441,058 | 8/1995 | Farced | 128/898 |
| 5,444,874 | 8/1995 | Samelian et al. | 2/159 |
| 5,447,490 | 9/1995 | Fula et al. | 601/40 |
| 5,454,438 | 10/1995 | Gates | 128/845 |
| 5,466,215 | 11/1995 | Lair et al. | 602/21 |
| 5,468,220 | 11/1995 | Sucher et al. | 602/21 |
| 5,476,439 | 12/1995 | Robinson | 601/40 |
| 5,478,306 | 12/1995 | Stoner | 602/40 |

Primary Examiner—Richard J. Apley
Assistant Examiner—Denise Pothier

[57] ABSTRACT

This invention relates to a finger restraint device to be worn by sufferers of hand and wrist injuries such as carpal tunnel syndrome, tendinitis, arthritis, and wrist sprain. The device comprises a finger restraining system in the form of a finger, hand and wrist covering which will support the wearer's fingers in a curled position, or to provide a core around which the fingers would normally grasp and be restrained by the covering. This places flexor and extensor tendons in a state of isotonic tension, and promotes a natural position with alignment of the wrist and tendons, ligaments, nerves, and blood vessels in the hand and wrist.

10 Claims, 7 Drawing Sheets

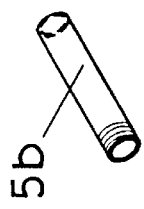
Fig. 5
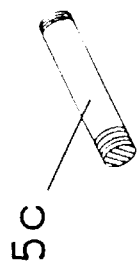
Fig. 5A
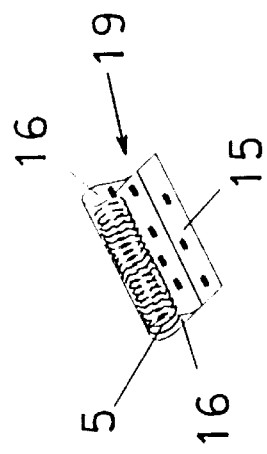
Fig. 5B
Fig. 5C
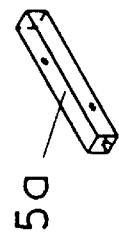
Fig. 5D
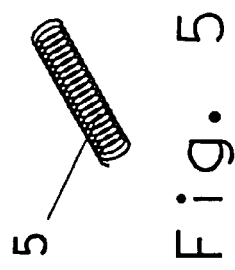
Fig. 5E
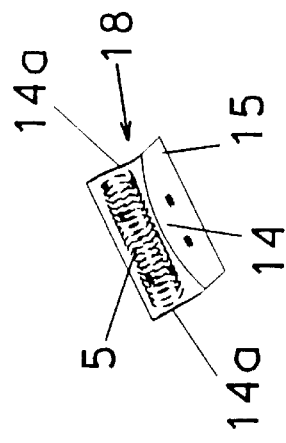
Fig. 5F
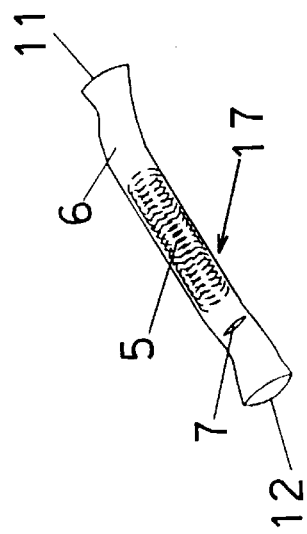

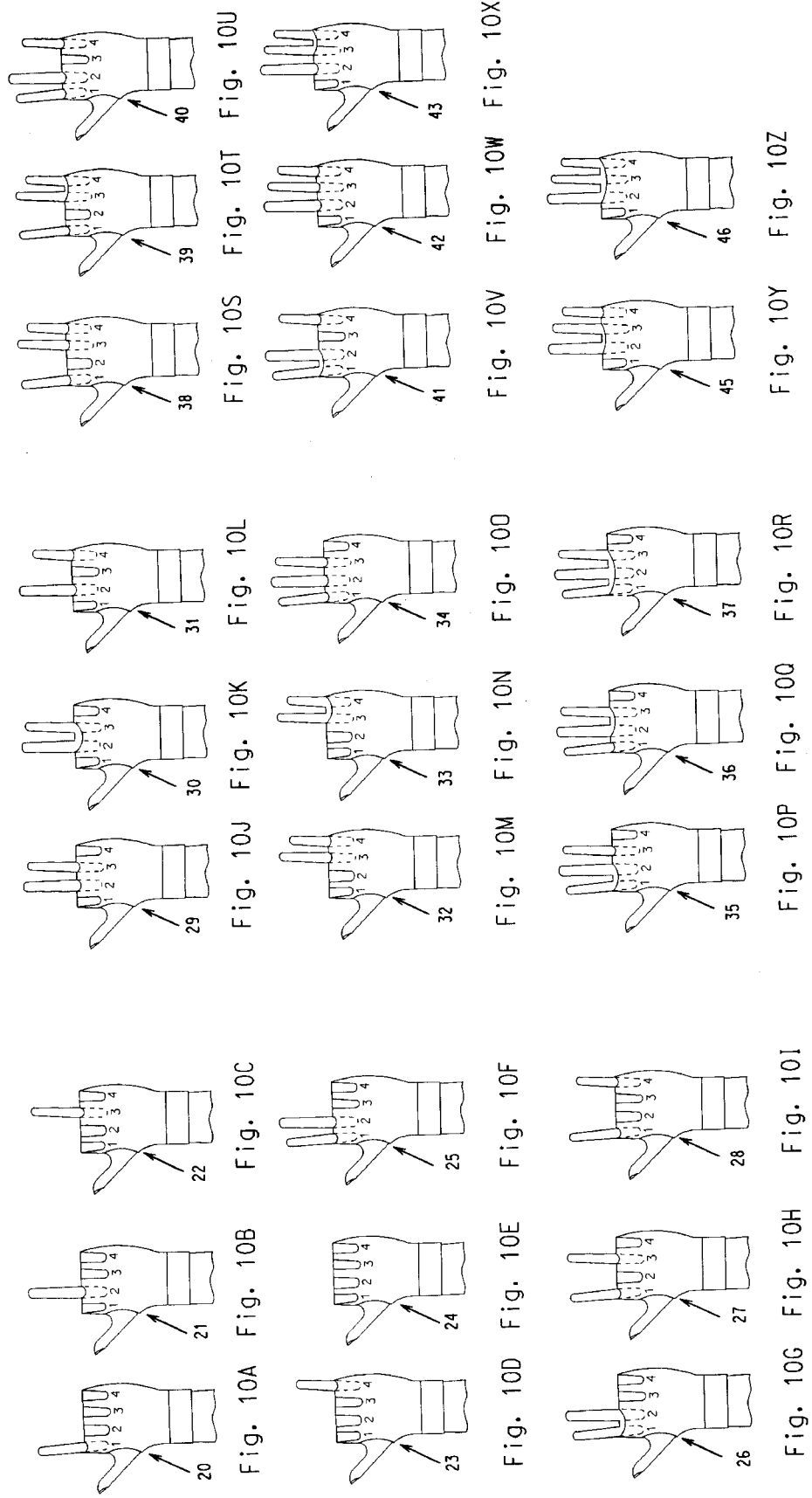

PHYSIOLOGY BASED WRIST SUPPORT

CROSS REFERENCE TO RELATED APPLICATIONS

This application claims the benefit of U.S. Provisional Application 60/016,854, filed May 3, 1996.

BACKGROUND OF THE INVENTION

1. Field of the Invention

This invention relates to the field of medical devices for treatment, and alleviation of symptoms of carpal tunnel syndrome, arthritis, tendinitis, and wrist sprain.

Common methods of treatment of these injuries and to alleviate symptoms are to restrict movement or immobilize the wrist using splits or external compression thus reducing trauma caused by bending the wrist. Prior art devices allow the fingers to move and flex. This means tendons, and ligaments can rub against nerves, bone structures, and blood vessels that may be further injured. This inappropriate movement may exacerbate the existing injury because the wrist is restrained from assuming a natural position.

Dr. Emil Pascarelli, "Repetitive Strain Injury", states that the use of rigid braces can interfere with the proper directional growth of scar tissue.

Dr. David Rumpel (Contra Costa Times Feb. 1, 1994) reported that devices used to restrain wrist movement while at the same time allow the fingers to flex and move did not reduce carpal tunnel pressure, and could actually increase the risk of carpal tunnel injury in some people.

The same thing can be said for tendinitis, and wrist sprains. Braces prevent the wrist from bending, but make no allowance for natural movement and normal position of the wrist's internal parts.

Surgery, an invasive action, has been used to relieve carpal tunnel symptoms however it is often only temporary relief from carpal tunnel injuries.

Without some form of wrist restraint these injures can be further exacerbated by the tendency of individuals to sleep with their hands in a fetal drop position. These situations further inflame the damaged tissue in the hand, and wrist.

This invention pertains to a finger restraining device designed to produce natural wrist position and alignment of tendons, nerves, and blood vessels passing thru the carpal tunnel area of the hand. It improves on prior art because it is more comfortable to wear, and improves on the immobilization of the internal structures of the hand and wrist.

The wrist and hand area contain many parts that are subject to injury. These include bone structures, nerves, blood vessels, tendons, and ligaments. Injuries to the hand and wrist include arthritis, repetitive stress injury (carpal tunnel syndrome), tendinitis, and sprains.

People suffering from these afflictions experience stiffness, tingling, numbness, loss of strength, and paraesthesia in their hands and fingers. This often disturbs their sleep causing them to awake in pain.

Arthritis is different from the others listed and its symptoms are frequently treated using warmth, moisture, and compression to provide temporary relief from pain and stiffness. Prior art devices include heating pads, and thermal gloves designed to compress the fingers, palm, and wrist. These devices do not address one of the real causes of stiff fingers. As people age their tendons tend to shrink during periods of non-use such as sleeping or resting. This shrinking is what creates some of the stiffness arthritis sufferers feel. Other disadvantages of these devices are that it is difficult to keep one's hand on a heating pad while sleeping, and gloves require a person to give up the tactile sense of feeling in their finger tips.

Carpal tunnel syndrome, tendinitis, and wrist sprain are another category of injury.

2. Background Art

The following patents on this subject were reviewed, and found to be different from the proposed invention.

U.S. Pat. No. 5,466,215 (Lair) makes reference to restrictive splints, which prevent natural wrist and finger movements. It also stresses two motions that should be minimized during sleep in order to treat, or reduce symptoms of carpal tunnel injuries. These are fetal hand drop, and backflip of the hand. Lair further states that rigid devices that encompass the wrist can also produce additional pressure on nerves just below the skin surface that are proximal to the bone structure, and blood vessels. These devices are also uncomfortable to wear. Lair also cites the high incidence of non-compliance of wearing prior art restrictive devices because they are uncomfortable, and difficult to apply with one hand.

Wrist supports do have a high incidence of non-compliance of instructed use especially during sleep, and U.S. Pat. No. 5,417,645 (Lemmen) notes that existing devices are lumpy, stiff, or bulky, and that there is a need for a device that is comfortable to use.

U.S. Pat. No. 5,385,537 (Davini) states the "best way to recovery (for wrist injuries) is non-use." At present there are no existing devices that immobilize the internal structures of the wrist in a natural position and that also provide for immediate use of the wearer's fingers when necessary.

Stretching of connective tissue is also an important consideration when treating joint injuries. U.S. Pat. No. 5,468,220 (Sucher) declares that the most effective recovery devices for joint injuries are those that provide a long period of low force stretching of connective tissue, and which also produce the greatest amount of permanent elongation of connective tissue. Low force stretching is frequently accomplished thru exercises that open and close the hand. One such exercise device, U.S. Pat. No. 5,492,525 (Gibney), provides for active stretching exercise during waking hours however no devices exist until now that promote stretching during periods of sleep.

Bruckner et al. (U.S. Pat. No. 4,290,147), Portal (U.S. Pat. No. 2,284,300) and Gatley et al. (U.S. Pat. No. 1,554,807) disclose the state of art of various orthopedic hand wraps. Bruckner discloses the tubular hand wraps have two open ends and an internal core located on the interior of the hand wrap configured for gripping. However, Bruckner does not disclose or teach the internal core having a sling or that the internal core is removable. Portal discloses in FIGS. 6–9 a glove with one open end that includes a sling and an internal core attached to the interior of the tubular hand wrap. However, Portal does not disclose or teach having two open ends or that the internal core is removable. Gately discloses that it is known in the art to include a thumb slit in these type of gloves.

Helferich (U.S. Pat. No. D 259,955), McLaurin-Smith (U.S. Pat. No. 4,961,418) and Tucker (U.S. Pat. No. 1,227,700) disclose the state of the art of fabric, tubular hand wraps. McLaurin-Smith discloses a heat-retaining fabric. None of these references disclose or teach placing a sling with an internal core in the interior of the tubular wrap being configured to be gripped by the user.

Schiavitto (U.S. Pat. No. 3,703,171) discloses that it is known in the orthopedic art to have a tubular member that has one end with a smaller diameter than the other in order to fit over the varying diameter of limbs.

Shields (U.S. Pat. No. 5,217,029) and Owen (U.S. Pat. No. 3,774,242) disclose therapeutic gloves that include an open end and gripping a core on the interior of the wrap. However, these reference do not disclose or suggests including a sling with a core attached to the interior of the wrap.

Meldeau (U.S. Pat. No. 5,353,440), Mann (U.S. Pat. No. 4,977,890, and Shelly (U.S. Pat. No. 5,37,620) disclose hand braces that have an internal core with a sling that is configured to be gripped by the user it for treating various ailments. Meldeau discloses that the internal core is removable from the sling. However none of these references disclose or teach the sling being attached to the interior of a tubular wrap.

U.S. Pat. No. 4,531,241, Berger A glove designed to minimize transmission of vibrations from hand held devices to the palm and wrist. Not applicable to my invention.

U.S. Pat. No. 4,829,604, Allen et al. This device is an adjustable wristlet that provides external support to the wrist by tightening of an adjustable strap. Not applicable to my invention.

U.S. Pat. No. 4,850,341, Fabry et al. This is an open ended finger less glove having a pad to cushion and protect the median nerve area of the hand. Not applicable to my invention.

U.S. Pat. No. 4,883,073, Aziz This device uses a flexible substrate, and splints to limit the range of forward (fetal hand drop), and backward (backflip) movement of the wrist. Not applicable to my invention.

U.S. Pat. No. 4 899 763, Sebastian et al. This device uses external restraints to limit wrist motion. In this case it is inflated air chambers that provide the rigidity. Not applicable to my invention.

U.S. Pat. No. 4,941,460, Working This device fastens to the hand, and forearm and spans the wrist with a rigid piece to immobilize the wrist. Not applicable to my invention.

U.S. Pat. No. 5,003,967, McConnell This device forces the wearer's hand into a fist using a wrapping method. The wearer must unwrap their hand in order to use their fingers. Not applicable to my invention.

U.S. Pat. No. 5,014,689, Meunchen et al. This device uses external means to limit hand extension, and flexion, ulnar, and radial deviation. This device is a flexible cavity that envelopes the outstretched hand of the wearer. It has a means for uncovering the hand without removing it from the wearer. No means are used to immobilize the fingers in the form of a fist.

It does not have any means to force the fingers to curl, nor does it have an insert for gripping. The wearer must pull on a flap in order to uncover the hand, whereas my invention has an open end and allows the wearer immediate uncovering of their fingers. Not applicable to my invention.

U.S. Pat. No. 5,058,573, Hess et al. This is an elastic sleeve with a thumb hole to be used as a bandage for the hand. It has no provisions for curling the fingers into a fist. Not applicable to my invention.

U.S. Pat. No. 5,152,740, Harkensee et al. This device is an inflatable bladder that fits into the palm of the wearer. At the recommended 20 PSI pressure, the bladder becomes a rigid tube pressing against the straps on the dorsal side of the hand. does not restrain the fingers in a curled position, and is attached to the hand using straps and hook and loop fasteners. It is designed to support the bones in the palmar region. The wearer must deflate the bladder to remove the device to utilize their hands. Not applicable to my invention.

U.S. Pat. No. 5,160,314, Peters This device is a sleeve with a thumb loop, and removable stay. It keeps the wearer's wrist immobile in a fixed position. Not applicable to my invention.

U.S. Pat. No. 5,203,766, Carter et al. This device is a splint made of rigid or semi rigid materials, pins with pivot points, and metal. It is designed to immobilize the wrist in a set position. It fastens to the forearm, and hand to span the wrist joint. Not applicable to my invention.

U.S. Pat. No. 5,205,812, Wasserman This device is a rigid splint, It has a hand engagement feature that is designed to prevent the fingers from curling. It also immobilizes the wrist. Not applicable to my invention.

U.S. Pat. No. 5,254,078, Carter et al. This is a rigid device requiring adjustable opposing plates which restrict wrist movement while the fingers can be moved. Not applicable to my invention.

U.S. Pat. No. 5,256,136, Sucher This device uses contoured, and rigid supports to hold the extended fingers back, and position the wrist, and thumb in order to stretch the transverse carpal ligament and enlarge the carpal canal, and relieve pressure on the median nerve.

My new invention positions the fingers forward in a normal fist position. Not applicable to my invention.

U.S. Pat. No. 5,358,471, Klotz This has rigid side pieces that are uncomfortable to the wearer who may lay on their hand. It has a hand grip for preventing the fingers to close into a fist. My invention forces the fingers to close normally, and has no rigid sides. Not applicable to my invention.

U.S. Pat. No. 5,370,606, Martel et al. This device has finger holes for all digits.

It is a fingerless glove with no provision for curling the wearer's fingers into a fist. Not applicable to my invention.

U.S. Pat. No. 5,376,066, Phillips et al. This device positions the wrist in a fixed flexion position. This device has one finger opening for each digit. It holds the wrist in an abnormal position when the wearer is moving the fingers, and gripping objects. Not applicable to my invention.

U.S. Pat. No. 5,385,537, Davini This device is a wrist strap. Davini does cite that the "best way to recovery (of wrist injuries) is non-use," however his device is not applicable to my invention.

U.S. Pat. No. 5,397,296, Sydor et al. This contains wraps, and stays for positioning the wrist as if it were a splint, and is not applicable to my invention.

U.S. Pat. No. 5,409,451, Daneman This invention serves as a splint immobilizing the wrist while the fingers are allowed to move. Not applicable to my invention.

U.S. Pat. No. 5,413,553, Downes This invention demonstrates that it is possible to have devices that do not require supporting of the wrist. It differs in that it has holes for all fingers, It uses non-elastic material on the dorsal side of the hand, and holds the wrist in flexion position. Downes cites the importance of, and the need for non-invasive means for rehabilitative, and preventative devices. Not applicable to my invention.

U.S. Pat. No. 5,417,645, Lemmen declares the need for a device that is comfortable to use, and that existing devices surveyed are lumpy, stiff, or bulky. This device serves as a reminder of the correct wrist position but the wearer must be conscious to be reminded. This device forces the wrist into a cocked up position which can be abnormal for some finger activities. It also fastens over the wrist and forearm spanning the joint. Not applicable to my invention.

U.S. Pat. No. 5,421,811, More et al. The device is similar to other compression wraps except that it helps position the wearers wrist at an angle. It uses external means to limit the range of motion of the wrist while allowing the fingers to move. Not applicable to my invention.

U.S. Pat. No. 5,441,058, Fareed This device claims to create proper alignment in the carpal tunnel by compressing the forearm muscles. Not applicable to my invention.

U.S. Pat. No. 5,444,874, Samelian A hand covering designed for normal extended finger positions. Not applicable to my invention.

U.S. Pat. No. 5,447,490, Fula et al. A device designed to curl fingers but has no means for the wearer to use their restricted fingers without removing part of the device. Not applicable to my invention.

U.S. Pat. No. 5,454,380, Gates This device is a rigid container into which the wearer inserts their hand. Various devices such as a knife can be affixed to the container so the wearer does not need to bend their fingers to grip. Not applicable to my invention.

U.S. Pat. No. 5,466,215, Lair et al. This device uses a loop fastened to a wristlet to restrict downward movement of the wrist. The loop encompasses one or more fingers, and when properly worn limits downward motion of the hand. Not applicable to my invention.

U.S. Pat. No. 5,468,220, Sucher Sucher states the most effective recovery devices are those with the longest period of low force stretching that produces the greatest amount of permanent elongation of connective tissue.

This is a bracelet that applies pressure to the carpal tunnel area. It uses pressure to stretch the transverse carpal ligament and related or associated structures of the wrist. Not applicable to my invention.

U.S. Pat. No. 5,476,439, Robinson This device is a full fingered glove with means to externally restrain movement of individual fingers. Not applicable to my invention.

U.S. Pat. No. 5,478,306, Stoner This device is a wristlet positioned over the median nerve area of the wrist. Not applicable to my invention.

In light of the above art, it would not have been obvious to one skilled in the art at the time of the invention to make a tubular hand wrap with ends of varying diameter and to attach a sling with a removable core to the interior of the wrap.

A non-surgical and more natural solution to these situations is to use a device that does not place pressure on the wrist, provides for stretching the tendons passing thru the wrist, promotes natural position of the wrist, alignment of the tendons, ligaments, nerves, and blood vessels passing through the wrist. It should also reduce fetal hand drop, and wrist backflip. The device should be passive and produce results when a person is sleeping. It should be comfortable to wear and should allow the user immediate freedom to use their fingers. My invention accomplishes these criteria.

SUMMARY

The present invention eliminates the problems of earlier carpal tunnel devices because it does not artificially restrict movement of the wrist. It does not contain stiffeners which means the wearer will be more comfortable and will tend to wear it for longer periods of time. It also limits the flexibility of the wrist preventing extreme positions of fetal hand drop, and backflip.

Thus the present invention, which I am naming Sof*Brace, provides for a more natural therapeutic immobilization of the wrist internal parts without the use of rigid splints as stiffening devices.

Accordingly the objective of the present invention is to provide a wrist treatment device and finger restraining system that:

A. Does not place external compression on the wrist thus reducing pressure on nerves (i.e. median nerve) just below the skin surface B. Provides for low force stretching of tendons, by positioning the fingers in a fist like position C. Prevents extreme bending of the wrist forward or backward, D. Naturally positions, and immobilizes affected parts of the hand and wrist thus reducing irritation of injured internal tissue, E. Allows the wearer to sleep or rest comfortably thus increasing the chances of compliance with prescribed instructions, and F. Allows the wearer immediate tactile use of their fingers when necessary to perform simple hand and finger movements.

G. Promotes a more natural directional growth of scar tissue.

These objectives will be further explained in the drawings.

OPERATION OF THE DEVICE

This device is designed to be worn on the right or left hand. The wearer slips on the device and curls their fingers around the insert core which is in a sling or pouch. The wearer may alternately curl all fingers, any single finger, or other possible combinations of fingers around the insert, leaving the remaining fingers extended. This insert may be heated or cooled as prescribed. The device retains the fingers in a curled position which places the flexor, and extensor tendons in a state of isotonic tension. This tension limits extreme flexing of the wrist forward (fetal hand drop) and backward (backflip). This tension also promotes natural positioning of the wrist internal parts without the use of external rigid bracing devices such as plates, splints, rigid cuffs or elastic compression devices.

The device may be constructed from fabric or a combination of flexible material such as fabric, leather, plastic or magnetic material. The device may contain magnetic material as part of the hand wrap or as part of the internal core.

BRIEF DESCRIPTION OF THE DRAWINGS

FIGS. 5, 5A, 5B, 5C, 5D, 5E, and 5F show selected different assemblies of the internal insert core, and its encompassing fabric. FIG. 5D shows the hollow sling assembly (17).

FIGS. 10A through FIG. 10Z show different finger opening configurations for the distal end of the finger restraining device.

DESCRIPTION OF PREFERRED EMBODIMENTS

Figure 1:
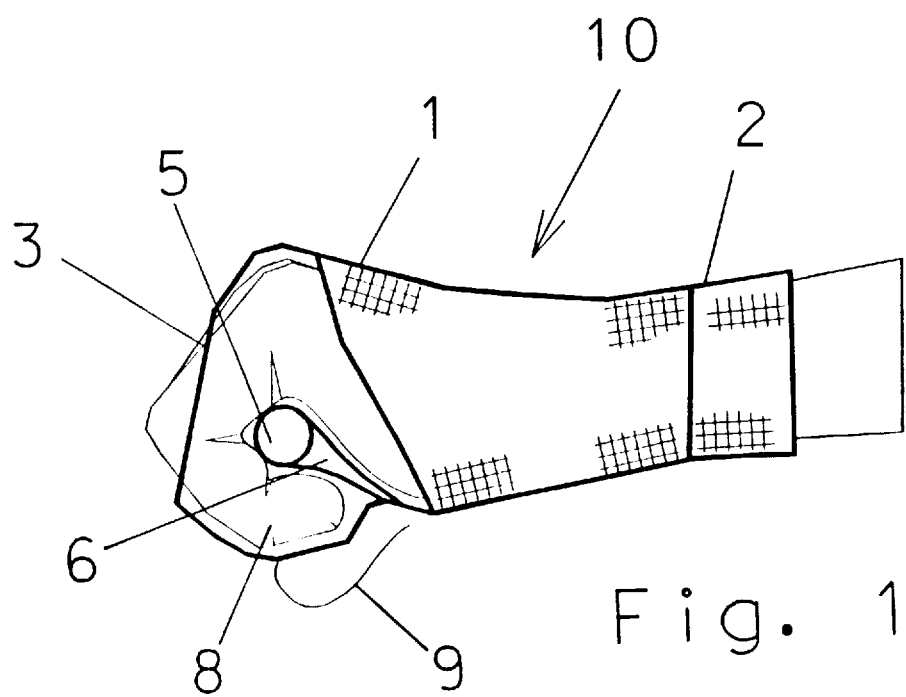
FIG. 1 is a side view of the finger restraining device on the left hand looking from the fifth finger toward the thumb.

FIG. 1 shows the finger restraining device (10) as it is worn on the left hand, and consists of a tube (1), open at both ends. Tube (1) has one end (2) for the cuff (2), and a second end for the fingers (3). The opening at the second end (3) of tube (1) may be slightly larger than the opening at the first end (2). Inside tube (1) there is a spring coil insert core (5) encompassed by hollow fabric sling (6). The ends of sling (6) are fastened to opposite sides of tube (1). The fingers are curled around insert core (5), and its encompassing hollow fabric sling (6). This view shows the left hand with the fifth finger (8) nearest the viewer, and the thumb (9) on the opposite side.

Figure 2:
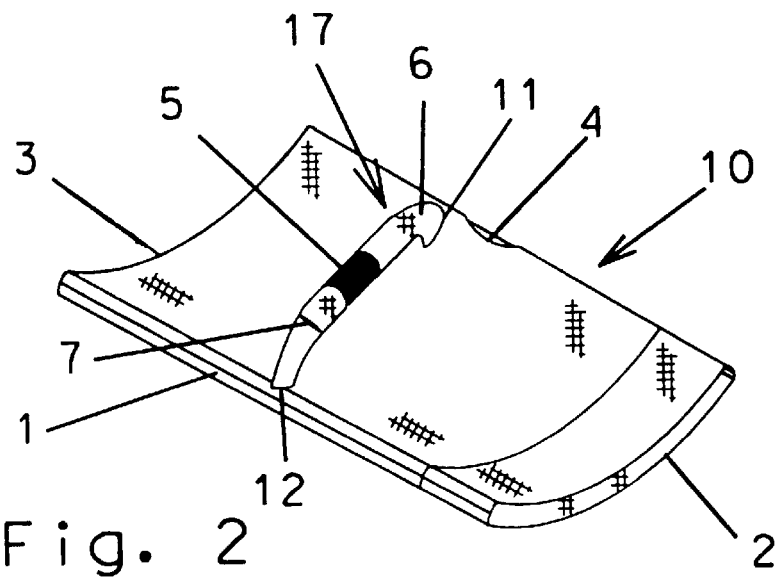
FIG. 2 is a perspective view of the finger restraining device turned inside out in order to display the internal parts.

FIG. 2 shows the finger restraining device (10) turned inside out, and consists of a tube (1) open at both ends. Tube (1) has one end for the cuff (2) and one end open for the fingers (3). The opening at the finger end (3) of the tube (1) is slightly larger than the opening at the cuff end (2). The side of tube (1) has a slit opening (4) which serves as a thumb hole. Inside tube (1) there is a spring coil insert core (5) encompassed by a hollow fabric sling (6). Encompassing hollow fabric sling (6) is attached to tube (1) at two places. The first attachment (11) is between thumb slit (4) and the distal end (3). The second attachment (12) is on the opposite side of tube (1) about half way between the distal end (3) and the proximal cuff end (2). The encompassing hollow fabric sling (6) has a button hole slit (7) for removing coil insert core (5). There is clearance between the inside of tube (1) and the encompassing hollow fabric sling (6) the wearer curls fingers of either hand around coil insert core (5) and encompassing hollow fabric sling spanning from attachment (11) to attachment (12). Insert core (5), encompassing hollow fabric sling (6), and button hole (7) comprise the insert core assembly (17).

Figure 3:
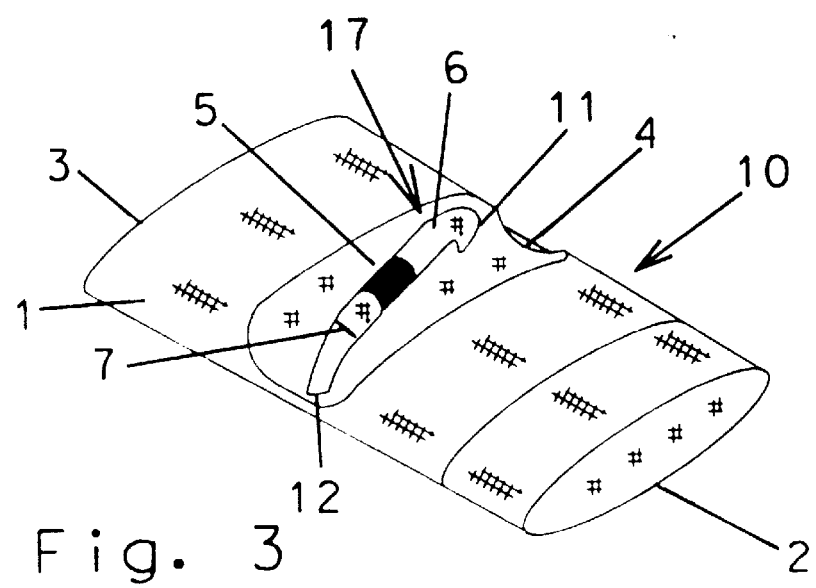
FIG. 3 shows the finger restraining device right side out and has a portion of the fabric cut away showing the internal parts.

FIG. 3 shows the finger restraining device (10) as it would appear from the outside, and has a cutaway view of the insert core (5), and its encompassing hollow fabric sling (6). Insert core (5), encompassing hollow fabric sling (6), and button hole (7) comprise the insert core assembly (17).

Figure 4A:
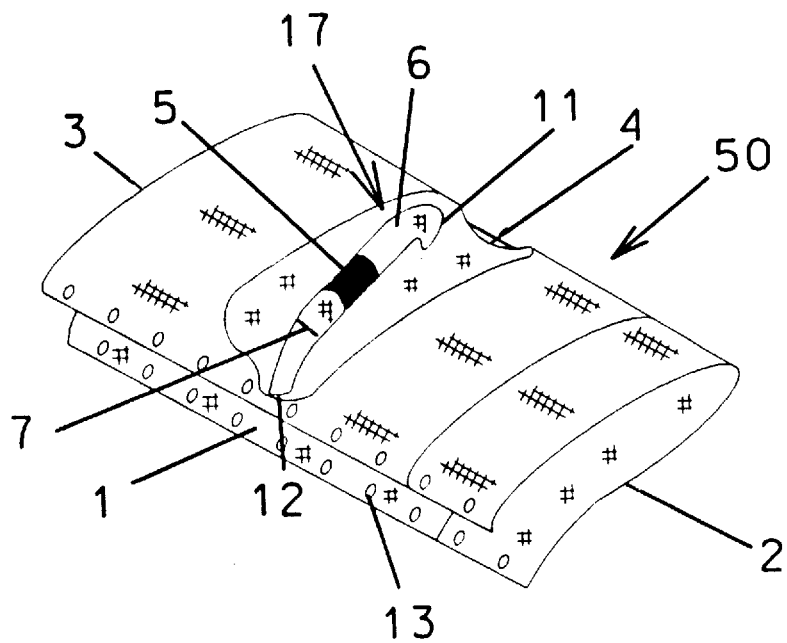
FIG. 4 shows the finger restraining device using laces as a means of closure, other closure means include a zipper FIG. 4C, and hook & loop fasteners FIG. 4B.
Figure 4B:
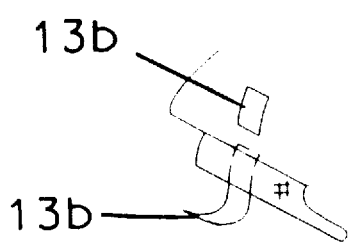
Figure 4C:
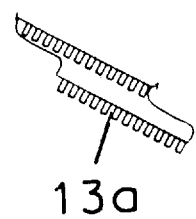

FIGS. 4A, 4B, and 4C show alternate means of closure to form a tube (1) for the finger restraining device (50). FIG. 4A shows laces (13), FIG. 4B shows hook and loop fasteners (13b), and FIG. 4C shows a zipper (13a).

FIGS. 5, 5A, 5B, and 5C show alternate insert core devices, a spring coil (5), a rectangular bar (5a), a hollow tube (5b), and a cylindrical bar (5c), that may be inserted into the encompassing fabric sling (6).

FIGS. 5D, 5E, and 5F show different insert core encompassing means, and means for installing and removing the insert core (5). FIG. 5D shows the preferred insert core assembly (17), prior to attaching to the finger restraining device (10) consisting of an encompassing hollow fabric sling (6) surrounding the insert core (5) and a button hole (7) for installing and removing the insert core (5). The ends (11 and 12) of the insert core assembly (17) are attached to the inside of finger restraining device (10). FIG. 5E shows a pouch (18) having opposing closed ends (14a), becoming a pocket (14) for installing and removing insert core (5), pouch (18) being fastened transversely to tube (10) at edge (15). FIG. 5F shows a sling (19) having open ends (16) for installing and removing insert core (5), the sling (19) to be fastened transversely to tube (10) at edge (15).

Figure 6:
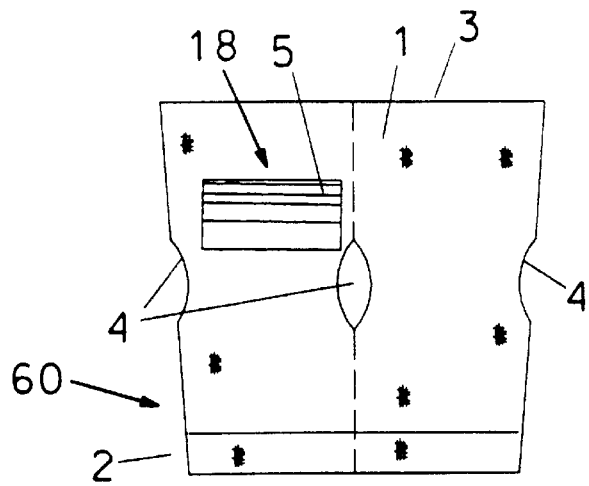
FIG. 6 shows a pattern for the finger restraining device having two thumb slits so it may be worn on either hand.

FIG. 6 consists of a pattern (60) for tube (1) having one pouch (18), and two thumb slits (4) allowing the finger restraining device (60) to be used on either hand.

Figure 7:
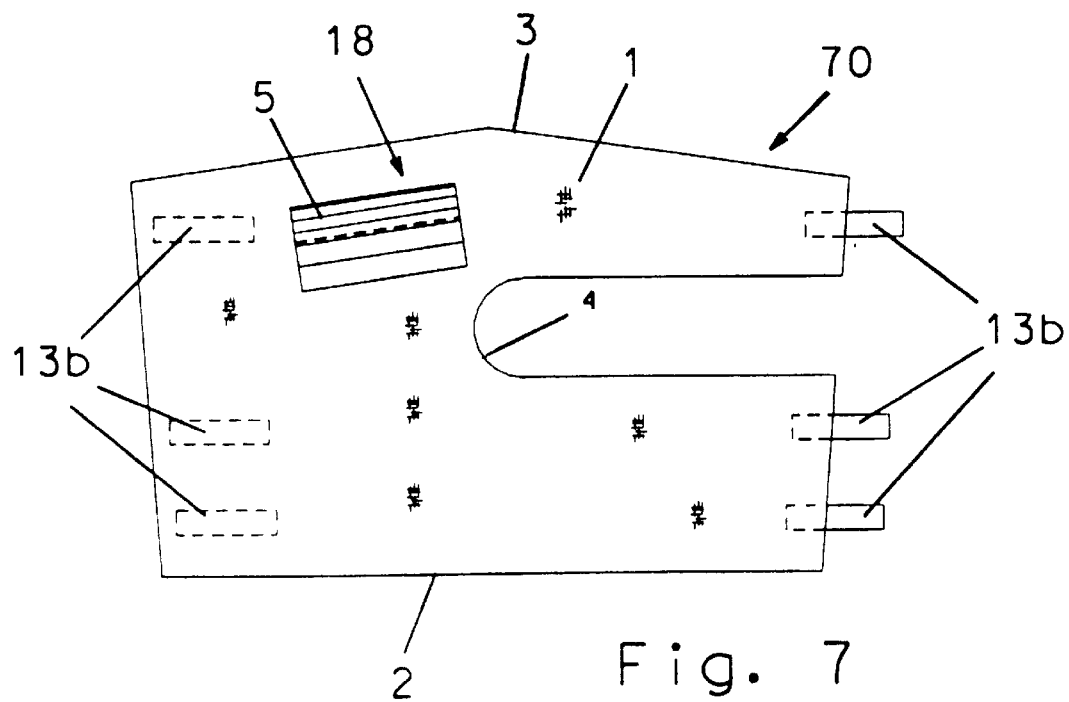
FIG. 7 shows a pattern for the finger restraining device when worn as a hand wrap, and shows a fastening means using hook & loop fasteners.

FIG. 7 shows a left hand pattern (70) for the finger restraining device (70) as a fabric hand wrap with hook & loop fasteners (13b). The pattern for the right hand would be a mirror image of pattern (70).

Figure 8:
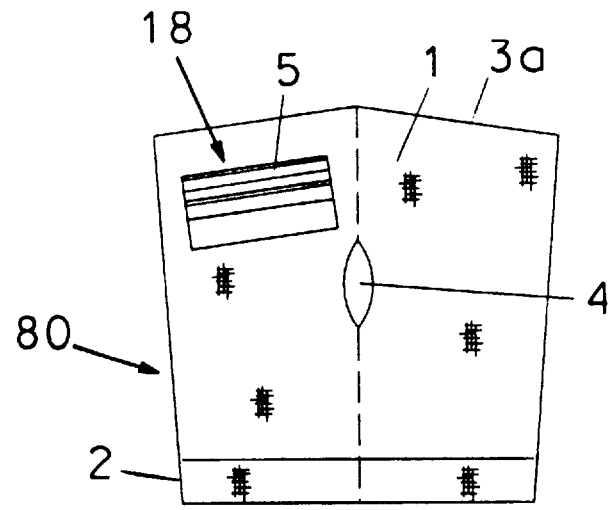
FIG. 8 shows a pattern for the finger restraining device for the left hand having one internal insert core containment assembly.

FIG. 8 shows a left hand pattern (80) having one insert core assembly pouch style (18), one thumb slit (4), and a tapered second or distal end (3a). The pattern for the right hand would be a mirror image of pattern (80).

Figure 9:
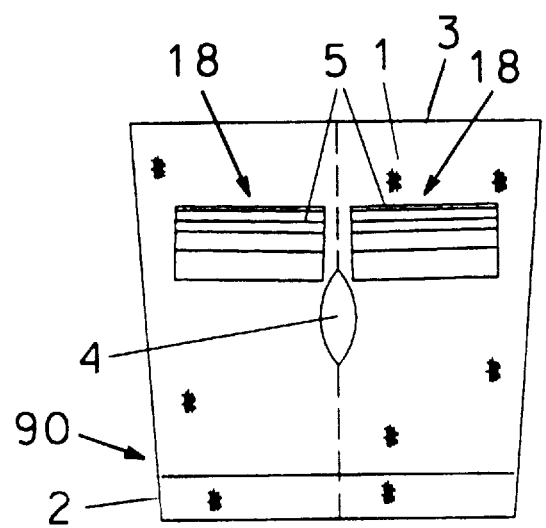
FIG. 9 shows a pattern for the finger restraining device that has two internal insert core containment assemblies so it may be worn on either hand.

FIG. 9 shows a pattern (90) having two pouch style insert core assemblies (18) on each side of a thumb slit (4) allowing the device to be used on either hand, by moving the core from one pouch to the other, whichever is in the position to be enclosed by the fingers.

FIGS. 10A through 10Z, show different configurations (20 thru 46) of the second or distal end (3) of finger restraining device (10).

It is to be understood that the present embodiments are illustrative and other modifications known to one skilled in the art, are intended to be included.

I claim:

1. A medical finger restraining device for supporting a user's hand comprising: (a) a fabric, tubular hand wrap having an open first end positionable at the wrist, an open second end positionable at the fingers, and a thumb slit, the first end having a first diameter, the second end having a second diameter, and the thumb slit located distal to the first end; (b) a hollow sling spanning transversely to the length of the tubular hand wrap attached to an interior of the tubular hand wrap and located between the thumb slit and the second end, said sling being positioned to be gripped by the fingers of the user; and (c) an insert core removably inserted into said sling.

2. The device of claim 1, said sling is a pocket and has an edge fastened transversely to the interior of said tubular hand wrap.

3. The device of claim 1 wherein the removable insert core has means for heating and cooling.

4. The finger restraining device of claim 1 wherein the first diameter is smaller than the second diameter or the first diameter is larger than the second diameter.

5. The finger restraining device of claim 1 wherein the tubular hand wrap and the sling are comprised of materials selected from the group consisting of cotton, nylon, Dacron, Lycra, wool, and rayon.

6. The finger restraining device of claim 1 wherein the insert core is comprised of a helical coil.

7. The finger restraining device of claim 1 further comprising a fastening means extending along the length of the hand wrap selected from the group consisting of stitches, laces, a zipper, and hook and loop fasteners.

8. The device of claim 1 wherein the core is comprised of materials selected from the group consisting of plastic, rubber, metal polyurethane foam, wood, and magnetic compounds.

9. The finger restraining device of claim 8 wherein the second end is positionable at a proximal end of the fingers, and is comprised of at least one finger hole adapted to receive the user's fingers.

10. A medical finger restraining device for supporting a user's hand comprising: (a) a fabric, tubular hand wrap having an open first end positionable at the wrist, an open positionable at the fingers, and thumb slits, the first end having a first diameter, the second end having a second diameter, and the thumb slits located distal to the first end, and opposed to each other along the length of the hand wrap; (b) a hollow sling spanning transversely to the length of the tubular hand wrap attached to an interior of the tubular hand wrap and located between the thumb slits and the second end, said sling being positioned to be gripped by the fingers of the user; and (c) an insert core removably inserted into said sling.

* * * * *